(12) United States Patent
Ackermann et al.

(10) Patent No.: US 8,097,634 B2
(45) Date of Patent: Jan. 17, 2012

(54) AZACYCLIC DERIVATIVES

(75) Inventors: Jean Ackermann, Riehen (CH); Aurelia Conte, Basel (CH); Daniel Hunziker, Moehlin (CH); Werner Neidhart, Hagenthal-le-Bas (FR); Matthias Nettekoven, Grenzach-Wyhlen (DE); Tanja Schulz-Gasch, Ziefen (CH); Stanley Wertheimer, Croton, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/082,433

(22) Filed: Apr. 8, 2011

(65) Prior Publication Data

US 2011/0257212 A1 Oct. 20, 2011

(30) Foreign Application Priority Data

Apr. 15, 2010 (EP) .................................... 10160030

(51) Int. Cl.
*A61K 31/438* (2006.01)
*C07D 471/10* (2006.01)
(52) U.S. Cl. .......................................... 514/278; 546/16
(58) Field of Classification Search ........................ None
See application file for complete search history.

(56) References Cited

FOREIGN PATENT DOCUMENTS

| WO | 2004/035550 | 4/2004 |
|----|-------------|--------|
| WO | 2006/087309 | 8/2006 |
| WO | 2007/067504 | 6/2007 |
| WO | 2010/130665 | 11/2010 |

OTHER PUBLICATIONS

PCT International Search, PCT/EP2011/055670 ( Jun 6, 2011).

*Primary Examiner* — Zinna Northington Davis
(74) *Attorney, Agent, or Firm* — George W. Johnston; Patricia S. Rocha-Tramaloni; Gene J. Yao

(57) ABSTRACT

The invention provides novel compounds having the general formula (I)

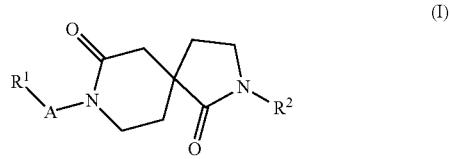

(I)

wherein $R_1$, $R_2$ and A are as described herein, compositions including the compounds and methods of using the compounds. The compounds inhibit hormone sensitive lipase (HSL) and may be used in the treatment of diabetes, metabolic syndrome, and obesity.

13 Claims, No Drawings

AZACYCLIC DERIVATIVES

PRIORITY TO RELATED APPLICATION(S)

This application claims the benefit of European Patent Application No. 10160030.2, filed Apr. 15, 2010, which is hereby incorporated by reference in its entirety.

FIELD OF THE INVENTION

The present invention relates to organic compounds useful for therapy or prophylaxis in a mammal, and in particular to inhibitors of hormone sensitive lipase (HSL) for the treatment of diabetes, metabolic syndrome and obesity.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess. The release of free fatty acids (FFA) from TAG is stimulated by catecholamines and regulated by hormones such as insulin, glucagon and epinephrine. The most important enzyme in WAT believed responsible for hormone regulated hydrolysis of triglyceride is hormone sensitive lipase (HSL).

Dysregulation of adipocyte lipolysis, resulting in elevated circulating non-esterified fatty acids (NEFA) is associated with obesity and co-morbidities including the development of type 2 diabetes. Obese or insulin resistant subjects have increased visceral adipose tissue depots. These depots contain elevated levels of HSL protein and exhibit enhanced lipolytic activity as they are resistant to the insulin-mediated suppression of lipolysis. This results in increased plasma levels of free fatty acids (FFA), which further exacerbates insulin resistance due to the accumulation of triglycerides in tissues other than WAT such as liver, pancreas and muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

Elevated FFAs are also associated with increased cardiovascular risk, including atherosclerosis and myocardial dysfunction. Furthermore high lipolytic activity and elevated FFAs lead to increased insulin resistance and hypertension in hypertensive rats. The FFA collect in the liver and lead to increased production of TAG, which are packaged into very low density lipoproteins (VLDL) which are secreted. Therefore, reducing the activity of HSL would decrease the release of FFA to the blood, thus limiting the supply of FFA to the liver for TAG synthesis. Thus, HSL inhibitors could have beneficial effects as treatment of nonalkoholic fatty liver disease (NAFLD) and nonalkoholic steatohepatitis (NASH).

SUMMARY OF THE INVENTION

The present invention provides novel compounds having the general formula (I)

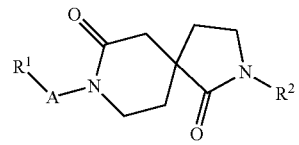

(I)

wherein
R[1] is selected from the group consisting of: alkyl, cycloalkyl, haloalkyl, piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl,
wherein said piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl may be substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl;
R[2] is selected from the group consisting of: phenyl, pyridinyl, pyrazinyl, pyrimidyl and pyridazinyl,
wherein said phenyl, pyridinyl, pyrazinyl, pyrimidyl and pyridazinyl may be substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl;
A is selected from the group consisting of: $-(CH_2)_n-$, $-C(O)-$ and $-S(O)_2-$; and
n is zero, 1 or 2;
or a pharmaceutically acceptable salt thereof.

The present invention also provides a pharmaceutical composition comprising a compound as described above and a therapeutically inert carrier.

DETAILED DESCRIPTION OF THE INVENTION

The present invention provides novel compounds having the general formula (I)

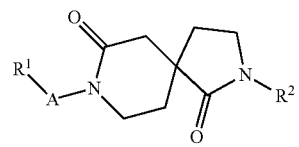

(I)

wherein
R[1] is selected from the group consisting of: alkyl, cycloalkyl, haloalkyl, piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl,
wherein said piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl may be substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl;

$R^2$ is selected from the group consisting of: phenyl, pyridinyl, pyrazinyl, pyrimidyl or pyridazinyl, wherein said phenyl, pyridinyl, pyrazinyl, pyrimidyl and pyridazinyl may be substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl;

A is selected from the group consisting of: —$(CH_2)_n$—, —C(O)— and —$S(O)_2$—; and n is zero, 1 or 2;

or a pharmaceutically acceptable salt thereof.

The term "alkyl", alone or in combination, signifies a straight-chain or branched-chain alkyl with 1 to 8 carbon atoms, in particular with 1 to 6 carbon atoms and further particular with 1 to 4 carbon atoms. Examples are methyl, ethyl, propyl, isopropyl, n-butyl, isobutyl, tert-butyl, n-pentyl, methylbutyl, dimethylpropyl, ethylpropyl, n-hexyl, methylpentyl, dimethylbutyl, trimethylpropyl and ethylmethylpropyl. Particular examples are methyl, ethyl, propyl, isopropyl, butyl, isobutyl and dimethylpropyl.

The term "cycloalkyl", alone or in combination, signifies a cycloalkyl ring with 3 to 8 carbon atoms and in particular with 3 to 6 carbon atoms. Examples are cyclopropyl, methylcyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. A particular example is cyclopropyl.

The term "hydroxy", alone or in combination, signifies the —OH group.

The term "hydroxyalkyl", alone or in combination, signifies an alkyl as defined before, wherein one or more hydrogen atoms are replaced by a hydroxy. Examples of hydroxyalkyl are hydroxymethyl, hydroxyethyl, hydroxypropyl, hydroxymethypropyl and dihydroxypropyl. Particular examples are hydroxyethyl and hydroxymethylpropyl.

The term "alkoxy", alone or in combination, signifies a group of the formula alkyl-O— in which the term alkyl has the previously given significance. Examples are methoxy, ethoxy, n-propoxy, isopropoxy, n-butoxy, isobutoxy, sec-butoxy and tert-butoxy.

The terms "halogen" and "halo", alone or in combination, signify fluorine, chlorine, bromine or iodine. Particular examples are fluorine or chlorine.

The term "haloalkyl", alone or in combination, signifies an alkyl as defined before, wherein one or more hydrogen atoms are replaced by a halogen. Examples of haloalkyl are fluoromethyl, difluoromethyl, trifluoromethyl, trifluoroethyl, trifluoromethylethyl or pentafluoroethyl. A particular example is trifluoroethyl.

The term "haloalkoxy", alone or in combination, signifies an alkoxy as defined before, wherein one or more hydrogen atoms are replaced by a halogen. Examples of haloalkoxy are fluoromethoxy, difluoromethoxy, trifluoromethoxy, trifluoroethoxy, trifluoromethylethoxy, trifluorodimethylethoxy or pentafluoroethoxy. Particular examples are trifluoromethoxy and trifluoroethoxy.

The term "carbonyl", alone or in combination, signifies the —C(O)— group.

The term "sulfonyl", alone or in combination, signifies the —$S(O)_2$— group.

The term "protecting group" refers to groups which are used to block the reactivity of functional groups such as amino groups or hydroxy groups. Examples of protecting groups are tert-butoxycarbonyl (Boc), benzyloxycarbonyl (Cbz), fluorenylmethoxycarbonyl (Fmoc) or benzyl (Bn). A particular protecting group is tert-butoxycarbonyl (Boc).

Cleavage of protecting groups can be done using standard methods known by the man skilled in the art such as hydrogenation or in the presence of an acid, e.g. HCl or TFA, or a base, e.g. triethylamine.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described above and pharmaceutically acceptable salts or esters thereof, in particular compounds according to formula (I) as described above and pharmaceutically acceptable salts thereof, more particularly compounds according to formula (I) as described above.

A further embodiment of the present invention are compounds according to formula (I) as described above, wherein $R^1$ is selected from the group consisting of: alkyl, cycloalkyl, haloalkyl, phenyl and pyridinyl, wherein said phenyl and pyridinyl may be substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl.

A particular embodiment of the present invention are compounds according to formula (I) as described above, wherein $R^1$ is alkyl or phenyl wherein said phenyl may be substituted with one to three halogen(s).

A particular embodiment of the present invention are compounds according to formula (I) as described above, wherein $R^1$ is alkyl or phenyl substituted with one to three halogen(s).

Also a particular embodiment of the present invention are compounds according to formula (I) as described above, wherein $R^1$ is alkyl.

A particular embodiment of the present invention are compounds according to formula (I) as described above, wherein $R^1$ is tert-butyl or 2,2-dimethylpropyl.

An alternative embodiment of the present invention are compounds according to formula (I) as described above, wherein $R^1$ is phenyl substituted with one to three halogen(s).

A particular embodiment of the present invention are compounds according to formula (I) as described above, wherein $R^1$ is chlorophenyl.

In a further embodiment of the present invention are compounds according to formula (I) as described above, wherein $R^2$ is phenyl or pyridinyl, wherein said phenyl and pyridinyl may be substituted with one to three substituents independently selected from the group consisting of: alkyl, cycloalkyl, cycloalkylalkyl, halogen, haloalkyl, hydroxy, hydroxyalkyl, alkoxy, alkoxyalkyl, haloalkoxy and hydroxyhaloalkyl.

In a particular embodiment of the present invention are compounds according to formula (I) as described above, wherein $R^2$ is phenyl substituted with one to three substituents independently selected from haloalkyl and haloalkoxy.

The present invention also relates to compounds according to formula (I) as described above, wherein $R^2$ is trifluoroethylphenyl or trifluoromethoxyphenyl.

A particular embodiment of the present invention are compounds according to formula (I) as described above, wherein A is —C(O)—.

A further particular embodiment of the present invention are compounds according to formula (I) as described above, wherein A is —S(O)$_2$—.

Also an embodiment of the present invention are compounds according to formula (I) as described above, wherein A is —(CH$_2$)$_n$—.

A particular embodiment of the present invention are compounds according to formula (I) as described above, wherein n is 1.

Particular examples of compounds of formula (I) are selected from the group consisting of:
8-Benzyl-2-(4-trifluoromethoxy-phenyl)-2,8-diaza-spiro [4.5]decane-1,7-dione;
8-Propyl-2-(4-trifluoromethoxy-phenyl)-2,8-diaza-spiro [4.5]decane-1,7-dione;
8-(2-Chloro-benzenesulfonyl)-2-(4-trifluoromethoxy-phenyl)-2,8-diaza-spiro[4.5]decane-1,7-dione;
8-(2-Methyl-propane-1-sulfonyl)-2-(4-trifluoromethoxy-phenyl)-2,8-diaza-spiro[4.5]decane-1,7-dione;
8-(3,3-Dimethyl-butyryl)-2-(4-trifluoromethoxy-phenyl)-2, 8-diaza-spiro[4.5]decane-1,7-dione;
8-Methyl-2-(4-trifluoromethoxy-phenyl)-2,8-diaza-spiro [4.5]decane-1,7-dione;
8-Ethyl-2-(4-trifluoromethoxy-phenyl)-2,8-diaza-spiro[4.5] decane-1,7-dione;
8-Butyl-2-(4-trifluoromethoxy-phenyl)-2,8-diaza-spiro[4.5] decane-1,7-dione;
8-(2,2-Dimethyl-propyl)-2-(4-trifluoromethoxy-phenyl)-2, 8-diaza-spiro[4.5]decane-1,7-dione;
8-(2-chlorophenylsulfonyl)-2-(4-(2,2,2-trifluoroethyl)phenyl)-2,8-diazaspiro[4.5]decane-1,7-dione;
8-(3,3-dimethylbutanoyl)-2-(4-(2,2,2-trifluoroethyl)phenyl)-2,8-diazaspiro[4.5]decane-1,7-dione; and
8-(3,3-dimethylbutanoyl)-2-(4-(2,2,2-trifluoroethoxy)phenyl)-2,8-diazaspiro[4.5]decane-1,7-dione.

Further particular examples of compounds of formula (I) are selected from the group consisting of:
8-(2,2-Dimethyl-propyl)-2-(4-trifluoromethoxy-phenyl)-2, 8-diaza-spiro[4.5]decane-1,7-dione;
8-(2-chlorophenylsulfonyl)-2-(4-(2,2,2-trifluoroethyl)phenyl)-2,8-diazaspiro[4.5]decane-1,7-dione; and
8-(3,3-dimethylbutanoyl)-2-(4-(2,2,2-trifluoroethyl)phenyl)-2,8-diazaspiro[4.5]decane-1,7-dione.

Processes for the manufacture of compounds of formula (I) are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

Compounds of formula (I) as described above are readily accessible as outlined in scheme 1 by heating compounds of formula (II) with a compound of general formula (III) and dimethylaluminium chloride in a solvent such as toluene at reflux temperature. The ring closure reaction can also be performed in dioxane as solvent and trimethylaluminium as organometallic reagent. This transformation allows access to compounds of general formula (I).

An alternative sequence to prepare compounds of general formula (I) and as outlined in scheme 1 consists of first performing the ring closure reaction on compounds of formula (IIa), by reacting them with a compound of general formula (III) and dimethylaluminium chloride as described above, to give compounds of general formula (Ia) which are then subsequently functionalized to give compounds of general formula (I). The transformation of compounds of general formula (Ia) to compounds of general formula (I) can be achieved on reaction with compounds of general formula (IV), wherein X is halogen, in particular Cl in case A is —C(O)— or —S(O)$_2$— and iodine or bromine in case A is —(CH$_2$)$_n$—, in a solvent such as THF and with a base such as sodium hydride or n-butyllithium at a temperature between −78° C. and RT.

Scheme 1

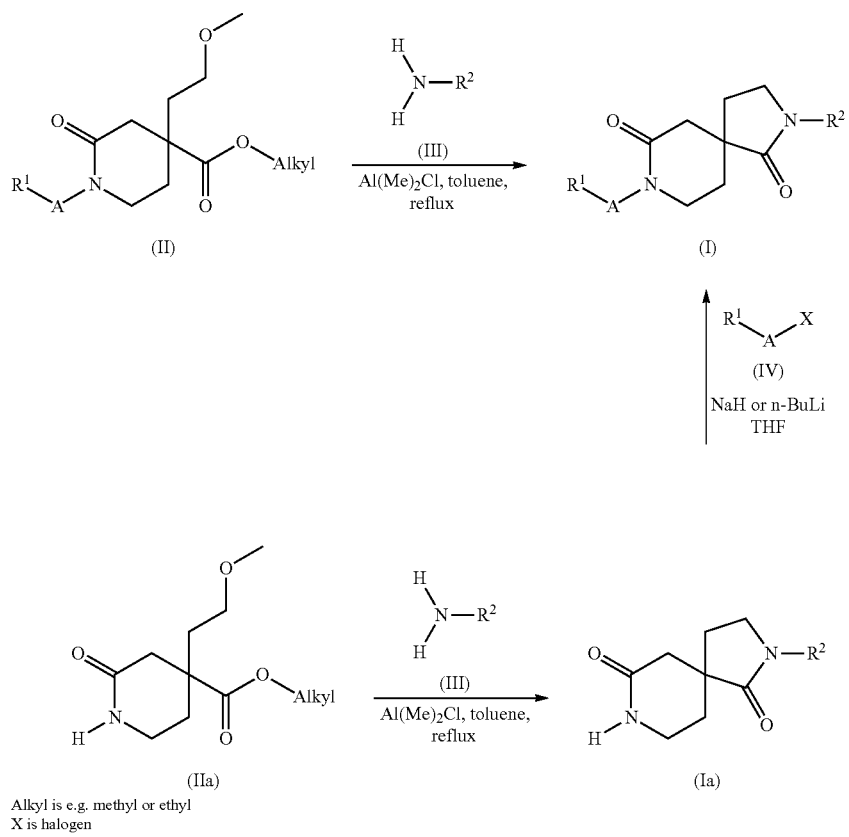

Alkyl is e.g. methyl or ethyl
X is halogen

The starting materials which are used in scheme 1 can be prepared from commercial compounds or compounds described in the literature applying general reaction procedures known in the art or outlined in scheme 2.

Thus, alkylation of compound (V), wherein protecting group is e.g Boc, with LDA as a base in a solvent such as THF at low temperature such as −5° C. with 1-bromo-2-methoxy-ethane gives rise to compounds of formula (VI). Compounds of general formula (VI) can then be selectively oxidized with RuCl₃/NaIO₄ in ethyl acetate/water at RT to give rise to compounds of general formula (VII). Subsequent removal of the protecting group, with an acid such as trifluoracetic acid in methylene chloride in the case protecting group is Boc, gives then rise to compounds of general formula (IIa). The conversion of compounds of formula (IIa) to (II) can be achieved similarly as described above on reaction with compounds of general formula (IV), wherein X is halogen, in particular Cl in case A is —C(O)— or —S(O)₂— and iodine or bromine in case A is —(CH₂)ₙ—, in a solvent such as THF and with a base such as sodium hydride or n-butyllithium at a temperature between −78° C. and RT.

Scheme 2

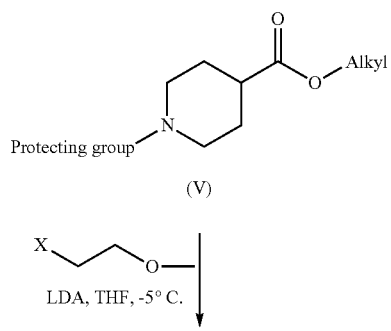

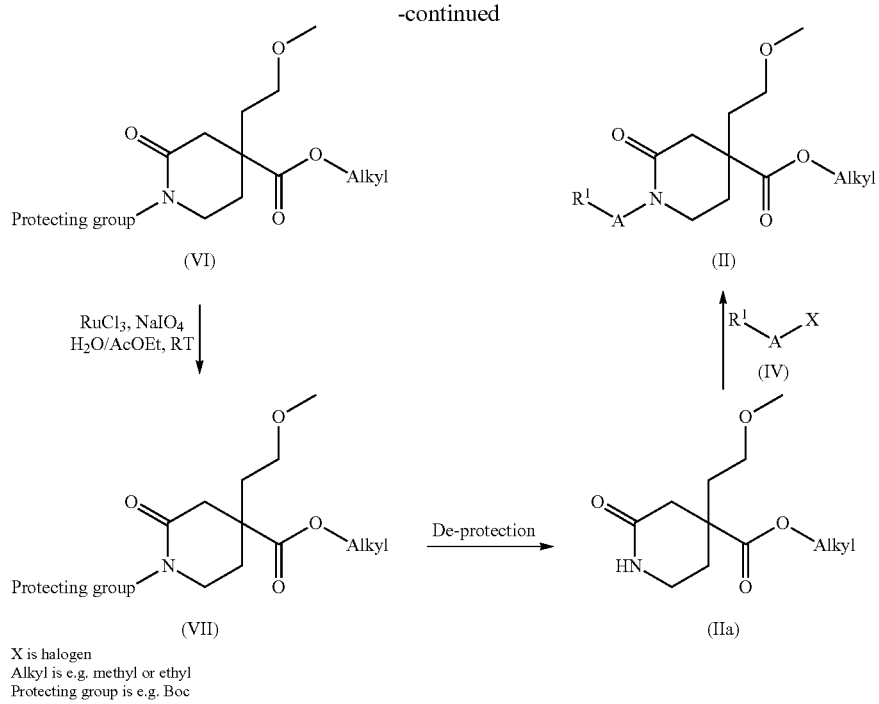

X is halogen
Alkyl is e.g. methyl or ethyl
Protecting group is e.g. Boc

Also an embodiment of the present invention is a process to prepare a compound of formula (I) as defined above

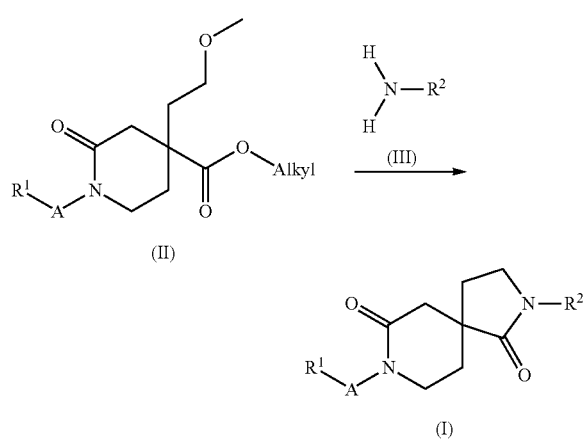

comprising the reaction of
a) a compound of formula (II) in the presence of a compound of formula (III);

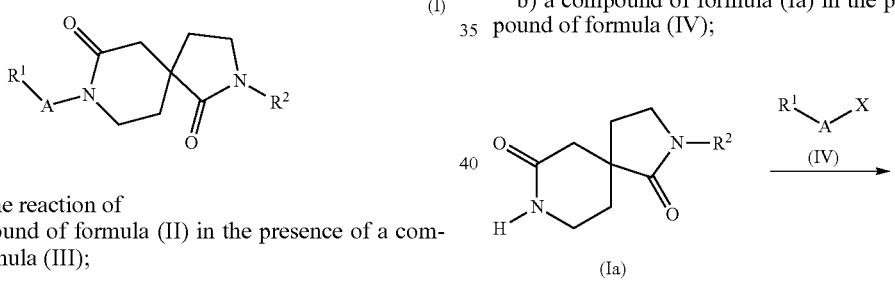

In particular in the presence of an organoaluminium reagent of formula Al(Alkyl)₃ or Al(Alkyl)₂X, particularly dimethylaluminium chloride or trimethylaluminium, in a solvent, particularly toluene, at a temperature comprised between RT and reflux of solvent, particularly at reflux temperature of toluene, wherein R¹, R² and A are as defined above and X is halogen, particularly chlorine;
or
b) a compound of formula (Ia) in the presence of a compound of formula (IV);

In particular in the presence of a base, particularly sodium hydride or n-butyllithium, in a solvent, particularly THF, at a temperature comprised between −78° C. and RT, wherein R¹, R² and A are as defined above and X is halogen, particularly chlorine in case A is —C(O)— or —S(O)₂—, and iodine or bromine in case A is —(CH₂)ₙ—.

Particular intermediates are selected from
4-(2-Methoxy-ethyl)-piperidine-1,4-dicarboxylic acid 1-tert-butyl ester 4-ethyl ester;
4-(2-Methoxy-ethyl)-2-oxo-piperidine-1,4-dicarboxylic acid 1-tert-butyl ester 4-ethyl ester;
4-(2-Methoxy-ethyl)-2-oxo-piperidine-4-carboxylic acid ethyl ester;
2-(4-Trifluoromethoxy-phenyl)-2,8-diaza-spiro[4.5]decane-1,7-dione;

4-(2-Methoxy-ethyl)-2-oxo-1-propyl-piperidine-4-carboxylic acid ethyl ester;

2-(4-(2,2,2-trifluoroethyl)phenyl)-2,8-diazaspiro[4.5]decane-1,7-dione; and 2-(4-(2,2,2-trifluoroethoxy)phenyl)-2,8-diazaspiro[4.5]decane-1,7-dione.

A further object of the present invention comprises a compound according to formula (I) as described above, when manufactured according to any one of the described processes.

Also an object of the present invention are compounds according to formula (I) as described above for use as therapeutically active substance.

Likewise an object of the present invention are pharmaceutical compositions comprising a compound according to formula (I) as described above and a therapeutically inert carrier.

Also an object of the present invention are compounds according to formula (I) as described above for the preparation of a medicament for the treatment or prophylaxis of illnesses which are caused by disorders associated e.g. with the enzyme hormone-sensitive lipase.

A particular embodiment of the present invention are compounds according to formula (I) as described above for the preparation of a medicament for the treatment or prophylaxis of diabetes, metabolic syndrome, dyslipidemia, atherosclerosis or obesity.

Also a particular embodiment of the present invention are compounds according to formula (I) as described above for the preparation of a medicament for the treatment or prophylaxis of cardiovascular diseases, myocardial dysfunction, inflammation, nonalkoholic fatty liver disease or nonalkoholic steatohepatitis.

A further particular embodiment of the present invention are compounds according to formula (I) as described above for the preparation of medicaments for the treatment or prophylaxis of diabetes.

Also a further particular embodiment of the present invention are compounds according to formula (I) as described above for the preparation of medicaments for the treatment or prophylaxis of diabetes Type II.

The present invention also relates to the use of a compound according to formula (I) as described above for the preparation of a medicament for the treatment or prophylaxis of diabetes, metabolic syndrome, dyslipidemia, atherosclerosis or obesity.

Also an embodiment of the present invention is the use of a compound according to formula (I) as described above for the preparation of a medicament for the treatment or prophylaxis of cardiovascular diseases, myocardial dysfunction, inflammation, nonalkoholic fatty liver disease or nonalkoholic steatohepatitis.

A particular embodiment of the present invention is the use of a compound according to formula (I) as described above for the preparation of medicaments for the treatment or prophylaxis of diabetes.

A further particular embodiment of the present invention is the use of a compound according to formula (I) as described above for the preparation of medicaments for the treatment or prophylaxis of diabetes Type II.

Also an object of the invention is a method for the treatment or prophylaxis of diabetes, metabolic syndrome, dyslipidemia, atherosclerosis or obesity, which method comprises administering an effective amount of a compound according to formula (I) as described above.

Also an embodiment of the present invention is a method for the treatment or prophylaxis of cardiovascular diseases, myocardial dysfunction, inflammation, nonalkoholic fatty liver disease or nonalkoholic steatohepatitis, which method comprises administering an effective amount of a compound according to formula (I) as described above.

A particular embodiment of the present invention is a method for the treatment or prophylaxis of diabetes, which method comprises administering an effective amount of a compound according to formula (I) as described above.

A further particular embodiment of the present invention is a method for the treatment or prophylaxis of diabetes Type II, which method comprises administering an effective amount of a compound according to formula (I) as described above.

Assay Procedures

Production of Human full length Hormone Sensitive Lipase-His[6]:

1) Cloning: cDNA was prepared from commercial human brain polyA+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the *E. coli* strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His[6], 48 hr., containing 25 μM E-64. Cell count: $1.78 \times 10^{10}$ cells/ml, 90% viable.

Cells were thawed. On ice, cells were suspended in Base Buffer containing 10% glycerol, 25 mM Tris-Cl, 300 mM NaCl, 10 mM imidazole, 10 mM 2-mercaptoethanol, 2 μg pepstatin/ml, 2 μg leupeptin/ml, 2 μg antipain/ml, pH 8.0 at 4° C. in a final volume of 475 ml with 3.75×107 cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 μm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 μm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 μm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) enzyme inhibition assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes).

3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Examples | HSL hum IC$_{50}$ (uM) |
|---|---|
| 1 | 0.27 |
| 2 | 0.25 |
| 3 | 0.03 |
| 4 | 0.16 |
| 5 | 0.11 |
| 6 | 6.02 |
| 7 | 0.81 |
| 8 | 0.1 |
| 9 | 0.08 |
| 10 | 0.03 |
| 11 | 0.06 |
| 12 | 0.14 |

Compounds of formula (I) and their pharmaceutically acceptable salts or esters thereof as described above have IC$_{50}$ values between 0.0001 uM and 1000 uM, particular compounds have IC$_{50}$ values between 0.001 uM and 500 uM, further particular compounds have IC$_{50}$ values between 0.001 uM and 5 uM. These results have been obtained by using the foregoing HSL enzyme inhibition assay (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention, the compounds of formula (I) and their pharmaceutically acceptable salts can be used for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

8-Benzyl-2-(4-trifluoromethoxy-phenyl)-2,8-diaza-spiro[4.5]decane-1,7-dione

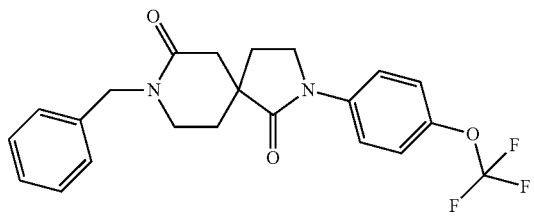

Step A): 4-(2-Methoxy-ethyl)-piperidine-1,4-dicarboxylic acid 1-tert-butyl ester 4-ethyl ester

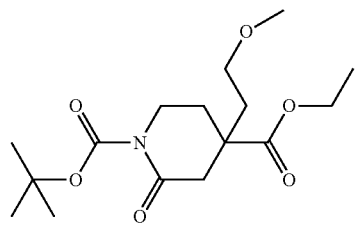

LDA (2M solution in THF/heptane/ethylbenzene, 24.48 ml, 0.049 mol) was added under an argon atmosphere to THF (150 ml) at −5° C., piperidine-1,4-dicarboxylic acid 1-tert-butyl ester 4-ethyl ester (6.3 g, 6 ml) in THF (100 ml) was then added dropwise and the mixture was stirred for 2 hour at 0° C. Then 1-bromo-2-methoxy-ethane (6.8 g) was added at 0° C. and the mixture was stirred overnight at RT. The solvent was evaporated off, the residue partitioned between AcOEt and water. The layers were separated, the organic layer was washed with brine, dried over sodium sulphate and then concentrated to give 4-(2-methoxy-ethyl)-piperidine-1,4-dicarboxylic acid 1-tert-butyl ester 4-ethyl ester (8 g) as a brown oil which was essentially pure and used in the next step without further purification. MS (ESI): 216.3 [(M-Boc)H$^+$].

Step B): 4-(2-Methoxy-ethyl)-2-oxo-piperidine-1,4-dicarboxylic acid 1-tert-butyl ester 4-ethyl ester

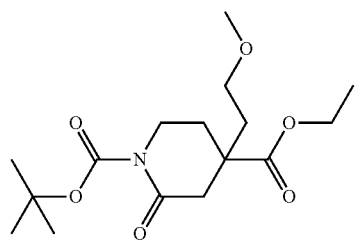

4-(2-Methoxy-ethyl)-piperidine-1,4-dicarboxylic acid 1-tert-butyl ester 4-ethyl ester (13 g) in AcOEt (300 ml) was added at RT under an argon atmosphere to a vigorously stirred solution of RuCl$_3$×H2O (1.71 g) and NaIO$_4$ (44.078 g) in water (300 ml). This mixture was vigorously stirred 30 minutes at RT. Then water and AcOEt were added and the layers were separated. The organic layer was washed with water and brine, dried over magnesium sulphate and concentrated to give the crude product as brown oil (8.78 g) which was used in next reaction step without further purification. MS (ESI): 352.17 (M+Na)$^+$ and 230.13 [(M-C$_5$H$_8$O$_2$)H$^+$]

Step C): 4-(2-Methoxy-ethyl)-2-oxo-piperidine-4-carboxylic acid ethyl ester

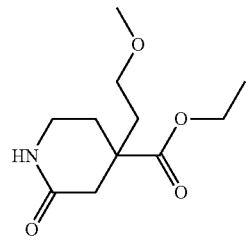

4-(2-Methoxy-ethyl)-2-oxo-piperidine-1,4-dicarboxylic acid 1-tert-butyl ester 4-ethyl ester (8.7 g) dissolved in dichloromethane (300 ml) under an argon atmosphere was treated with trifluoroacetic acid (60.32 g, 39.11 ml) and stirred for 3 hours at RT. The reaction mixture was then concentrated in vacuo, the residue dissolved in AcOEt, which was then washed with 3M aqueous NaOH, brine and dried over magnesium sulphate. The solvent was removed in vacuo and the residue was chromatographed on silica gel (acetone/CH$_2$Cl$_2$, gradient 0 to 10%) to give the desired product as light brown viscous oil (1.49 g). MS (ESI): 230.13 (MH$^+$).

Step D): 2-(4-Trifluoromethoxy-phenyl)-2,8-diaza-spiro[4.5]decane-1,7-dione

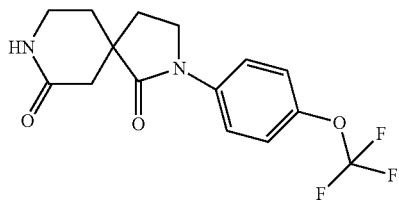

4-(2-Methoxy-ethyl)-2-oxo-piperidine-4-carboxylic acid ethyl ester (2 g) and 4-(trifluormethoxy)aniline (3.09 g) were dissolved in toluene (100 ml) under an argon atmosphere at RT, dimethylaluminium chloride in hexane (1 molar, 39.25 ml) was added and the mixture was refluxed for 8 hours. The reaction mixture was then cooled to RT, diluted with AcOEt, quenched with water (9 ml), dried over MgSO$_4$, filtered and the solvent was evaporated off. The residue was adsorbed on silica gel and purified by flash chromatography on silica gel (acetone/CH$_2$Cl$_2$, gradient from 0 to 40%) to give 2-(4-trifluoromethoxy-phenyl)-2,8-diaza-spiro[4.5]decane-1,7-dione as light brown solid. MS (ESI): 329.1 (MH$^+$).

Step E): 8-Benzyl-2-(4-trifluoromethoxy-phenyl)-2,8-diaza-spiro[4.5]decane-1,7-dione To NaH (0.093 g, 55% suspension in oil), washed twice with pentane (each 4 ml), was added at RT under an argon atmosphere 2-(4-trifluoromethoxy-phenyl)-2,8-diaza-spiro[4.5]decane-1,7-dione (0.093 g) in THF (15 ml) and the mixture was stirred at RT for 20 minutes. Then benzyl bromide (0.073 g) was added in one portion and the mixture was stirred for 3 h at RT until completion of conversion according to mass spectroscopy. The reaction was quenched with 3M aqueous HCl (a few drops), the solvent was evaporated off and the residue adsorbed on silica gel and chromatographed on silica gel (AcOEt/heptane, gradient from 0 to 50%) to give the desired product (0.046 g) as white solid. MS (ESI): 419.15 (MH+).

Example 2

8-Propyl-2-(4-trifluoromethoxy-phenyl)-2,8-diaza-spiro[4.5]decane-1,7-dione

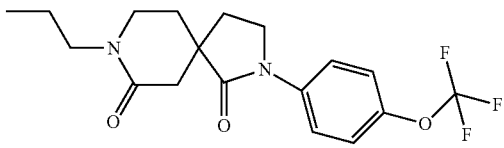

Step A): 4-(2-Methoxy-ethyl)-2-oxo-1-propyl-piperidine-4-carboxylic acid ethyl ester

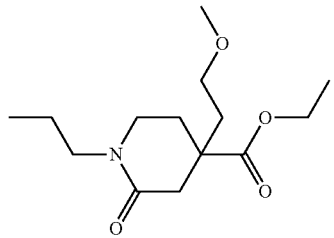

To NaH (0.38 g, 55% suspension in oil), washed twice with pentane (each 6 ml), was added at RT under an argon atmosphere 4-(2-methoxy-ethyl)-2-oxo-piperidine-4-carboxylic acid ethyl ester (0.4 g) in THF (15 ml) and the mixture was stirred at RT for 5 minutes. Then 1-bromopropane (1.073 g) was added in one portion and the mixture was stirred over night at RT until completion of conversion according to mass spectroscopy. The reaction was quenched with 3M aqueous HCL (5 drops) and the reaction mixture was then partitioned between AcOEt and water. The layers were separated, the organic layer was washed with brine and dried over magnesium sulphate. The solvent was evaporated off to give the desired product as a light yellow semi-solid (0.2 g) which was directly used in the next step without further purification. MS (ESI): 272.3 (MH+).

Step B): 8-Propyl-2-(4-trifluoromethoxy-phenyl)-2,8-diaza-spiro[4.5]decane-1,7-dione 4-(2-Methoxy-ethyl)-2-oxo-1-propyl-piperidine-4-carboxylic acid ethyl ester (0.205 g) and 4-(trifluormethoxy)aniline (0.268 g) were dissolved in toluene (15 ml) under an argon atmosphere at RT. Dimethylaluminium chloride in hexane (1 molar in hexane, 3.02 ml) was added and the mixture was refluxed over night. The reaction mixture was then cooled to RT, water (1 ml) was added and the mixture was stirred at RT for 15 minutes. The solvent was removed in vacuo, the residue adsorbed on silica gel and purified by flash chromatography on silica gel (eluents: AcOEt/CH$_2$Cl$_2$, gradient from 0 to 50% then with AcOEt/heptane: 70%) to give the desired material (0.072 g) as a viscous light yellow oil. MS (ESI): 371.2 (MH−).

Example 3

8-(2-Chloro-benzenesulfonyl)-2-(4-trifluoromethoxy-phenyl)-2,8-diaza-spiro[4.5]decane-1,7-dione

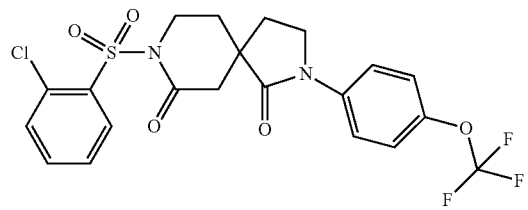

2-(4-Trifluoromethoxy-phenyl)-2,8-diaza-spiro[4.5]decane-1,7-dione (0.105 g), product of example 1 step D), was dissolved in dry THF (10 ml), cooled to −78° C. under an argon atmosphere, treated dropwise with n-butyllithium (1.6 molar solution in hexanes, 0.22 ml) and then stirred for 20 minutes at −78° C. 2-Chlorobenzenesulfonyl chloride (0.074 g) in THF (2 ml) was then added dropwise, the mixture was stirred 15 minutes at −78° C., the cooling bath was removed and stirring was continued for further 75 minutes, allowing the temperature of the reaction mixture to rise to RT. The reaction mixture was then concentrated in vacuo, the residue adsorbed on silica gel and chromatographed on silica gel (AcOEt/heptane, gradient from 0 to 30%) to give the desired product (0.051 g) as an off-white solid. MS (ESI): 503.0 (MH−).

Example 4

8-(2-Methyl-propane-1-sulfonyl)-2-(4-trifluoromethoxy-phenyl)-2,8-diaza-spiro[4.5]decane-1,7-dione

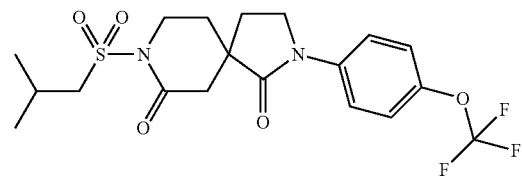

This material was prepared as a white solid in analogy to example 3 from 2-(4-trifluoromethoxy-phenyl)-2,8-diaza-spiro[4.5]decane-1,7-dione, product of example 1 step D), and 2-methyl-propane-1-sulfonyl chloride. MS (ESI): 466.1 (M+NH$_4$)+.

Example 5

8-(3,3-Dimethyl-butyryl)-2-(4-trifluoromethoxy-phenyl)-2,8-diaza-spiro[4.5]decane-1,7-dione

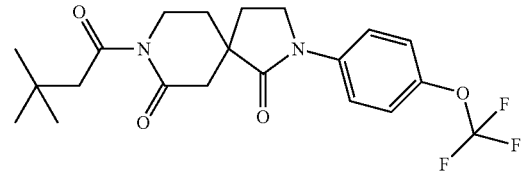

This material was prepared as a white solid in analogy to example 3 from 2-(4-trifluoromethoxy-phenyl)-2,8-diaza-

Example 6

8-Methyl-2-(4-trifluoromethoxy-phenyl)-2,8-diaza-spiro[4.5]decane-1,7-dione

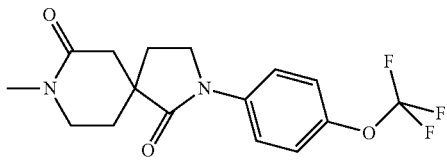

This material was prepared as a yellow semi-solid in analogy to example 1 step E) from 2-(4-trifluoromethoxy-phenyl)-2,8-diaza-spiro[4.5]decane-1,7-dione and methyl iodide. MS (ESI): 343.1 (MH+).

Example 7

8-Ethyl-2-(4-trifluoromethoxy-phenyl)-2,8-diaza-spiro[4.5]decane-1,7-dione

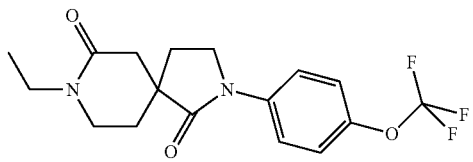

This material was prepared as a off-white solid in analogy to example 1 step E) from 2-(4-trifluoromethoxy-phenyl)-2,8-diaza-spiro[4.5]decane-1,7-dione and ethyl iodide. MS (ESI): 357.1 (MH+).

Example 8

8-Butyl-2-(4-trifluoromethoxy-phenyl)-2,8-diaza-spiro[4.5]decane-1,7-dione

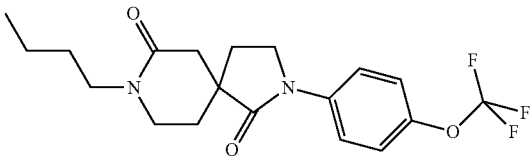

This material was prepared as a white solid in analogy to example 1 step E) from 2-(4-trifluoromethoxy-phenyl)-2,8-diaza-spiro[4.5]decane-1,7-dione and 1-bromo-butane. MS (ESI): 385.1 (MH+).

Example 9

8-(2,2-Dimethyl-propyl)-2-(4-trifluoromethoxy-phenyl)-2,8-diaza-spiro[4.5]decane-1,7-dione

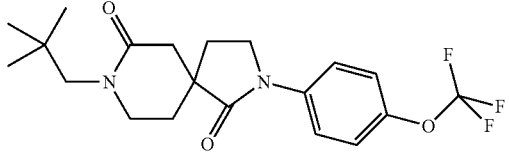

This material was prepared as a off-white semi-solid in analogy to example 1 step E) from 2-(4-trifluoromethoxy-phenyl)-2,8-diaza-spiro[4.5]decane-1,7-dione and neopentyl iodide. MS (ESI): 399.1 (MH+).

Example 10

8-(2-chlorophenylsulfonyl)-2-(4-(2,2,2-trifluoroethyl)phenyl)-2,8-diazaspiro[4.5]decane-1,7-dione

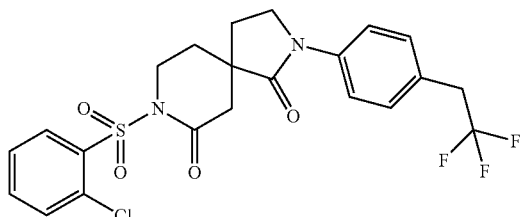

Step A): 2-(4-(2,2,2-trifluoroethyl)phenyl)-2,8-diaza-spiro[4.5]decane-1,7-dione

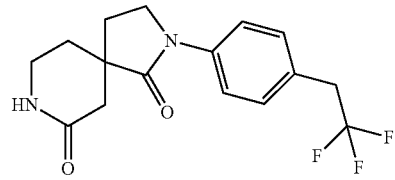

This material was prepared as a white solid (0.72 g) in analogy to example 1 step D) from 4-(2-methoxy-ethyl)-2-oxo-piperidine-4-carboxylic acid ethyl ester (1.03 g), dimethylaluminium chloride (0.9 M in hexane, 20 ml) and 4-(2,2,2-trifluorethyl)aniline (1.2 g). MS (ESI): 327.13 (MH−).

Step B): 8-(2-chlorophenylsulfonyl)-2-(4-(2,2,2-trifluoroethyl)phenyl)-2,8-diazaspiro[4.5]decane-1,7-dione This material was prepared as a white solid in analogy to example 3) from 2-(4-(2,2,2-trifluoroethyl)phenyl)-2,8-diazaspiro[4.5]decane-1,7-dione and 2-chlorobenzenesulfonyl chloride. MS (ESI): 501.08 (MH+).

Example 11

8-(3,3-dimethylbutanoyl)-2-(4-(2,2,2-trifluoroethyl)phenyl)-2,8-diazaspiro[4.5]decane-1,7-dione

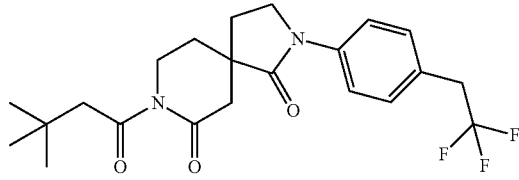

This material was prepared as a white solid in analogy to example 3) from 2-(4-(2,2,2-trifluoroethyl)phenyl)-2,8-diazaspiro[4.5]decane-1,7-dione, product of example 10 step A), and 3,3-dimethyl-butyryl chloride. MS (ESI): 425.2 (MH+).

--- spiro[4.5]decane-1,7-dione, product of example 1 step D), and 3,3-dimethyl-butyryl chloride. MS (ESI): 427.1 (MH+).

Example 12

8-(3,3-dimethylbutanoyl)-2-(4-(2,2,2-trifluoroethoxy)phenyl)-2,8-diazaspiro[4.5]decane-1,7-dione

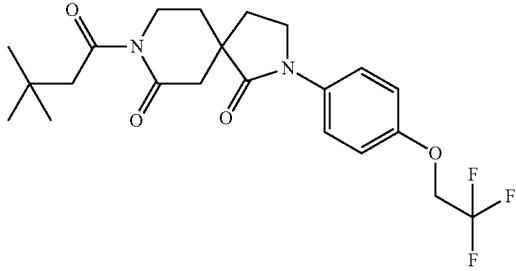

Step A): 2-(4-(2,2,2-trifluoroethoxy)phenyl)-2,8-diazaspiro[4.5]decane-1,7-dione

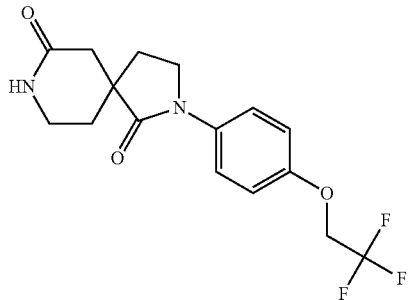

This material was prepared as a light brown solid (0.685 g) in analogy to example 1 step D) from 4-(2-methoxy-ethyl)-2-oxo-piperidine-4-carboxylic acid ethyl ester (1 g), dimethylaluminium chloride (1 M in hexane, 17.4 ml) and 4-(2,2,2-trifluoro-ethoxy)-phenylamine (1.25 g). MS (ESI): 343.12 (MH$^+$).

Step B) 8-(3,3-dimethylbutanoyl)-2-(4-(2,2,2-trifluoroethoxy)phenyl)-2,8-diazaspiro[4.5]decane-1,7-dione This material was prepared as a white solid in analogy to example 3) from 2-(4-(2,2,2-trifluoroethoxy)phenyl)-2,8-diazaspiro[4.5]decane-1,7-dione and 3,3-dimethyl-butyryl chloride. MS (ESI): 441.19 (MH$^+$).

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I)

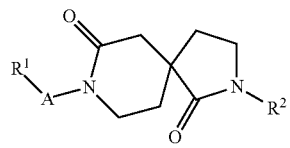

wherein $R^1$ is selected from the group consisting of: alkyl, cycloalkyl, haloalkyl, piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl, wherein said piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl may be substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl;

$R^2$ is selected from the group consisting of: phenyl, pyridinyl, pyrazinyl, pyrimidyl and pyridazinyl, wherein said phenyl, pyridinyl, pyrazinyl, pyrimidyl and pyridazinyl may be substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl;

A is selected from the group consisting of: —(CH$_2$)$_n$—, —C(O)— and —S(O)$_2$—; and n is zero, 1 or 2;

or a pharmaceutically acceptable salt thereof.

2. A compound according to claim 1, wherein $R^1$ is selected from the group consisting of:

alkyl, cycloalkyl, haloalkyl, phenyl and pyridinyl, wherein said phenyl and pyridinyl may be substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl.

3. A compound according to claim 1, wherein $R^1$ is selected from the group consisting of:

alkyl or phenyl wherein said phenyl may be substituted with one to three halogen(s).

4. A compound according to claim 1, wherein $R^1$ is alkyl or phenyl substituted with one to three halogen(s).

5. A compound according to claim 1, wherein $R^2$ is phenyl or pyridinyl,
   wherein said phenyl and pyridinyl may be substituted with one to three substituents independently selected from the group consisting of: alkyl, cycloalkyl, cycloalkylalkyl, halogen, haloalkyl, hydroxy, hydroxyalkyl, alkoxy, alkoxyalkyl, haloalkoxy and hydroxyhaloalkyl.

6. A compound according to claim 1, wherein $R^2$ is phenyl substituted with one to three substituents independently selected from haloalkyl and haloalkoxy.

7. A compound according to claim 1, wherein A is —C(O)—.

8. A compound according to claim 1, wherein A is —S(O)$_2$—.

9. A compound according to claim 1, wherein A is —(CH$_2$)$_n$—.

10. A compound according to claim 1, wherein n is 1.

11. A compound according to claim 1, selected from the group consisting of:
    8-Benzyl-2-(4-trifluoromethoxy-phenyl)-2,8-diaza-spiro[4.5]decane-1,7-dione;
    8-Propyl-2-(4-trifluoromethoxy-phenyl)-2,8-diaza-spiro[4.5]decane-1,7-dione;
    8-(2-Chloro-benzenesulfonyl)-2-(4-trifluoromethoxy-phenyl)-2,8-diaza-spiro[4.5]decane-1,7-dione;
    8-(2-Methyl-propane-1-sulfonyl)-2-(4-trifluoromethoxy-phenyl)-2,8-diaza-spiro[4.5]decane-1,7-dione;
    8-(3,3-Dimethyl-butyryl)-2-(4-trifluoromethoxy-phenyl)-2,8-diaza-spiro[4.5]decane-1,7-dione;
    8-Methyl-2-(4-trifluoromethoxy-phenyl)-2,8-diaza-spiro[4.5]decane-1,7-dione;
    8-Ethyl-2-(4-trifluoromethoxy-phenyl)-2,8-diaza-spiro[4.5]decane-1,7-dione;
    8-Butyl-2-(4-trifluoromethoxy-phenyl)-2,8-diaza-spiro[4.5]decane-1,7-dione;
    8-(2,2-Dimethyl-propyl)-2-(4-trifluoromethoxy-phenyl)-2,8-diaza-spiro[4.5]decane-1,7-dione;
    8-(2-chlorophenylsulfonyl)-2-(4-(2,2,2-trifluoroethyl)phenyl)-2,8-diazaspiro[4.5]decane-1,7-dione;
    8-(3,3-dimethylbutanoyl)-2-(4-(2,2,2-trifluoroethyl)phenyl)-2,8-diazaspiro[4.5]decane-1,7-dione; and
    8-(3,3-dimethylbutanoyl)-2-(4-(2,2,2-trifluoroethoxy)phenyl)-2,8-diazaspiro[4.5]decane-1,7-dione.

12. A compound according to claim 1, selected from the group consisting of:
    8-(2,2-Dimethyl-propyl)-2-(4-trifluoromethoxy-phenyl)-2,8-diaza-spiro[4.5]decane-1,7-dione;
    8-(2-chlorophenylsulfonyl)-2-(4-(2,2,2-trifluoroethyl)phenyl)-2,8-diazaspiro[4.5]decane-1,7-dione; and
    8-(3,3-dimethylbutanoyl)-2-(4-(2,2,2-trifluoroethyl)phenyl)-2,8-diazaspiro[4.5]decane-1,7-dione.

13. A pharmaceutical composition comprising a compound according to claim 1 and a therapeutically inert carrier.

* * * * *